United States Patent [19]
Sprokholt et al.

[11] Patent Number: 4,806,486
[45] Date of Patent: Feb. 21, 1989

[54] CALIBRATION LIQUID FOR ION-SPECIFIC ELECTRODES, PROCESS FOR PREPARING THEM AND THEIR APPLICATION

[75] Inventors: Ronald Sprokholt, Amsterdam; Alphons B. T. J. Boink, Zeist; Antonius H. J. Maas, Utrecht, all of Netherlands

[73] Assignee: Stichting Gastransport, Utrecht, Netherlands

[21] Appl. No.: 823,325

[22] Filed: Jan. 28, 1986

[30] Foreign Application Priority Data

Jan. 31, 1985 [NL] Netherlands ............ 8500266

[51] Int. Cl.$^4$ ............................................. G01N 31/00
[52] U.S. Cl. .......................................... 436/19; 436/8; 436/17; 436/18

[58] Field of Search ................ 436/8, 17, 18, 19, 11; 252/408.1

[56] References Cited

U.S. PATENT DOCUMENTS

| 3,629,142 | 12/1971 | Marbach | 436/19 |
| 3,682,835 | 8/1972 | Louderback | 436/8 |
| 4,363,633 | 12/1982 | Christiansen | 436/16 |
| 4,458,021 | 7/1984 | Herring | 436/11 |

Primary Examiner—Barry S. Richman
Assistant Examiner—T. J. Wallen
Attorney, Agent, or Firm—Watson, Cole, Grindle & Watson

[57] ABSTRACT

A calibration liquid, especially suitable for ion-selective electrodes, containing albumin. This solution is stable and prevents errors by junction potentials or unknown complexing with calcium.

17 Claims, No Drawings

CALIBRATION LIQUID FOR ION-SPECIFIC ELECTRODES, PROCESS FOR PREPARING THEM AND THEIR APPLICATION

BACKGROUND OF THE INVENTION

This invention relates to a calibration liquid for the determination of blood components by means of ion-selective electrodes.

Such determinations, in particular of pH, sodium, potassium and calcium, are performed in great numbers nowadays, and medical actions are often governed by their results. As such determinations are always comparative, the significance of their results is directly related to the quality of the solutions(s) used for calibrating the ion-selective electrodes. As the electrodes gradually drift away, or at least may do so, frequent calibration is desirable, if not necessary. Even without legal obligation, calibrating the electrodes will be done at least every day in many clinical laboratories.

Thus, a reliable and stable calibration liquid is essential. This was emphasized once more by R. A. Durst at a seminar on blood pH and gases, held in Utrecht on June 5 and 6, 1978 (see the Proceedings thereof, ed. by A. H. J. Maas (Utrecht University Press, March 1979)).

An attempt for such a calibration liquid is known from German patent application No. 3,024,044 and the corresponding U.S. Pat. No. 4,363,633. Herein solutions are described containing, besides sodium, potassium, calcium, chloride and optionally other inorganic cations, such as magnesium, as a buffer a partially neutralized nitrogen-containing organic sulfonic acid, which has the advantage of forming with calcium neither complexes nor precipitates. These buffered calibration solutions are stable, too.

However, they may still cause errors (and occasionally will certainly do so) because of the liquid junction potential which occurs at the junction (transition) between salt bridge and sample solution or calibration solution. The error can easily attain a value of 0.002 volts, corresponding to 8% difference in the measured concentration. Moreover, it is now realized that because of complex formation the activities of the above-mentioned cations are generally less than their concentrations, and this is especially true for calcium. Disregarding this phenomenon will result in lower cathode potentials, which may be misinterpreted as concentrations lower than those that actually exist. This latter phenomenon may result in quite sizable errors.

It is conceivable that blood plasma could function as a calibration liquid; it contains all the elements to be determined in blood and also all the additional components that might influence the measuring results. However, blood plasma does not keep. Even when carefully sterilized (for example, by sterile filtration) it is not stable, since, because of a residual lipase acid is liberated slowly and the pH gradually drifts away to lower values, influencing all other electrode potential readings.

SUMMARY OF THE INVENTION

It has now been discovered that all these troubles are eliminated with a stable calibration liquid containing sodium, potassium, calcium, chloride, a buffer and optionally other inorganic ions, which is characterized in that it additionally contains albumen in a concentration of from 20 to 200 g per liter.

It was discovered that such an albumen-containing solution will take away the error (residual liquid junction potential) between salt bridge and calibration solution or sample solution and will cause a constant, reproducible and known lowering of calcium activity, so that there are no doubts about the relevance of the potential readings.

Preferably, this solution contains about 70 g/liter (1.1. mole/l) of albumen.

The albumen will generally have originated from blood, especially bovine blood. Other qualities will also be satisfactory. Blood plasma solids, consisting substantially of albumins and globulins, will be satisfactory. Generally the albumin contains small amounts of sodium, potassium and calcium, which do not interfere.

Sodium, potassium, calcium and optionally magnesium may be provided for as the chlorides, calcium and magnesium optionally as carbonates, sodium optionally as bicarbonate. Additional chloride may be provided as dilute hydrochloride acid (HCl) or as tetramethyl ammonium chloride (TMA-Cl).

As buffering substance all known combinations that do not interfere with the ions present in solution or with their determination may be used. However, many of the known buffers form complexes or precipitates of calcium, and are therefore less suitable. This holds especially for the phosphate and citrate buffers. The partially neutralized nitrogen-containing organic sulfonic acids mentioned in German patent application No. 3,024,044 and U.S. Pat. No. 4,363,633 are very well suitable.

In particular, favourable results were obtained with 2-[4-(2-hydroxyethyl)piperazino]ethane sulfonic acid (Hepes) and N-[tris(hydroxymethyl)methyl]-2-aminoethane sulfonic acid (TES) partially neutralized with NaOH.

The concentrations of the above-mentioned components will be generally selected approximately at the values naturally occurring in blood, i.e. about $140.10^{-3}$M of Na, about $4.10^{-3}$M of K, $2.10^{-3}$M of Ca (50-75% of which in free, ionized form) and about $100.10^{-3}$M of Cl.

It is particularly favourable, however, to calibrate the electrodes on a series of three calibration solutions, one of them having the relevant concentrations at about the values of blood from a normal, healthy individual, one of them having these concentrations at about the lowest values that one might encounter, and one of them having these concentrations at about the highest values that one might encounter. By doing so, there will only be intrapolation and never extrapolation and there will always be a check on the relation between concentration and potential reading. The following set of calibrating solutions will be especially satisfactory:

| Component | low level | normal | high level |
|---|---|---|---|
| | concentrations in mmol/liter | | |
| $Na^+$ | 120 | 140 | 160 |
| $K^+$ | 3.0 | 4.2 | 6.0 |
| $Ca^{2+}$ total | 1.0 | 2.1 | 3.3 |
| free, ionized $Ca^{2+}$ | 0.75 | 1.25 | 1.75 |
| $Cl^-$ | 80 | 100 | 120 |
| pH | 7.2 | 7.4 | 7.6 |
| Total protein | 70 g/l | 70 g/l | 70 g/l |

The above concentrations include the contributions from buffer(s) and optional TMA-Cl.

It is also possible, and even highly preferable, to make this kind of solutions suitable for calibrating the $CO_2$ and $O_2$ determinations. On order to achieve this, the calibration liquid should also contain the bicarbonate ion $HCO_3'$ and it should eventually be tonometered (i.e. equilibrated with a gas mixture containing known amounts of $CO_2$ and $O_2$). Since the $CO_2/HCO_3'$ couple is a buffer per se in that case, the other buffer (HEPES, TES, or any other) may be omitted or diminished. At least, it is taken into account.

The invention also relates to solid material from which the specified solutions may be prepared. They correspond to the above-described solutions from which all the water has been removed. Such a material is easily kept and transported. It is an advantage that, due to the presence of salts, this dry composition (different from albumin) will dissolve quickly in water.

The invention also relates to a method for preparing calibration solutions suitable for calibrating the determinations of blood components. This process comprises dissolving the above-specified components in water, controlling their concentrations and the pH and adjusting the concentrations and the pH, if necessary or desired.

By preference, these calibration solutions are prepared as follows:

An albumin solution of known strength is started from which has a concentration considerably above the final concentration aimed at. The well-known biuret method is suitable for measuring the exact strength; the result of this determination controls the final volume to which the solution will be diluted. For example, an albumin solution of twice the eventual strength is made.

$Na'$, $K'$, $Ca_{tot}''$ and pH are also determined therein. The necessary amounts of K, total Ca and Cl are adjusted by adding KCl, $CaCl_2$ and NaCl (and/or TMA-Cl). If the solution is to contain $NaHCO_3$ it is added now. Next, the total amount of Na is adjusted by adding the sodium form of the selected buffer (e.g. Na-Hepes, which is the sodium salt of 2-[4-(2-hydroxyethyl)-piperazino]ethane sulfonic acid), and then the pH is adjusted by adding the acid form of that buffer, no additional cation being introduced.

Now, the concentration of ionized calcium (iCa) is determined (by means of a calcium specific electrode). If it is found to be too low, $CaCl_2$ is added, and if it it found to be too high, a calcium scavenger, such as ethylenediamine tetraacetic acid (EDTA), is added.

A final control of pH, protein, Na, K, iCa and $Ca_{tot}$ is performed, after which the solution is sterilized by filtration and bottled in glass vials under nitrogen gas or a mixture of nitrogen and carbon dioxide.

A dry composition from which a calibration solution may be made is conveniently prepared by evaporating a solution as above described to dryness, e.g. by freeze-drying. Alternatively the dry components are blended, monitoring in a similar way as when preparing a solution.

The invention also relates to the use of the above-described calibration solutions for an easy and reliable calibration of determinations of blood components. The manner in which this calibration is performed will be clear to the man of the art and need not be described in detail here.

The following examples serve as illustrations only.

EXAMPLE I

A solution of bovine serum albumin (Cohn fraction V) in twice distilled water containing about 140 g/l (2.2. mmol/l) of albumin and having a pH of 6.70–6.80 (at 37° C.) was started from. By analysis it was found to contain 14 mmol/l of Na, 0.25 mmol/l of K, 0.19 mmol/l of Ca and no detectable Cl.

From this solution a 5 ml samples was taken to make a pilot solution with a final volume of 10 ml having the desired protein concentration of 70 g/l. Furthermore this preparation was aimed at the normal level of the components. Therefore, the following additions were made:

K: $4.20 - 0.25 = 3.95$ mmol/l, i.e. 79 μl of 0.5M KCl solution iCa: already present was 0.38 mmol/l, ⅝ of which is estimated to be free, ionised. Added were 150 μl of 0.1M $CaCl_2$ solution.

Cl: $103 - (3.9 + 3.00) = 96$ mml/l, therefore 960 μl of 1M NaCl solution

Na: $142 - (96 + 14) = 32$ mmol/l, therefore 640 μl of 0.5M Na-Hepes solution.

pH: For a pH of 7.40 (Na-Hepes/Hepes) had to be 1.67, So 19.2 mmoles of Hepes or 390 μl of 0.5M Hepes solution had to be added.

Water to attain a final volume of 10 ml.

Measuring tCa, iCa, Na, K, Cl (in mmol/l) and pH showed:

tCa = 1.88 iCa = 1.13, therefore 60% of tCa was free, ionized $Ca^{2+}$

Na = 142

K = 4.2

Cl = 103 pH = 7.39 iCa = 1.13 mM  ⎫       0.60, thus 0.12 mM iCa or
tCa = 1.88 mM  ⎬  =    0.2 mM tCa had to be added
               ⎭

Now tCa had to be 2.1 mM/l so 0.2 mM/l $CaCl_2$ had to be added. Because of that Cl rose by 0.4 mM/l: $102.95 + 0.4 = 103.35$ mM/l.

So in a new pilot plant Cl had to be diminished, while keeping Na constant. Therefore the amount of NaCl was decreased and Na-Hepes was increased with an equal amount. More Na-Hepes caused a slight increase of the pH, which was not harmful in this case. Otherwise it would have been necessary to increase the amount of Hepes in order to maintain the desired pH, in this case at 7.40.

So there was occasion to adjust the NaCl concentration 1.0 mM lower and the Na-Hepes concentration 1.0 mM higher. The new pilot solution was made as follows:

5 ml of albumin stock solution

79 μl of 0.5M KCl

170 μl of 0.1M tCa

950 μl of 1M NaCl (Cl = $103 - 3.95 - 3.40 = 95.65$, rounded off 95 μM

660 μl of 0.5M Na-Hepes

390 μl of 0.5M Hepes

2751 μl of water, to make 10 ml

Measuring now showed:

tCa = 2.08 iCa = 1.25

Na = $14^2$

K = 4.2

Cl = $10^2$ pH = 7.406

Now a larger amount of calibration solution containing all the components in the desired concentrations would be prepared by multiplying the amounts for the second pilot solution with a constant factor. This new solution was flushed with nitrogen, sterilized by filtration under nitrogen through a "Millipore" filter (0.22 μm) and packing in glass vials, which were sealed.

EXAMPLE II

Following the above recipe of example I a series of three solutions was prepared (the only deviation being that for the "low level" solution no additional $CaCl_2$ had to be provided, but rather a few milliliters of 0.1M EDTA solution).

|  | low level | normal | high level |
| --- | --- | --- | --- |
| pH (at 37° C.) | 7.20 ± 0.02 | 7.40 ± 0.02 | 7.60 ± 0.02 |
| Na | 120 | 142 | 160 |
| K | 3.0 | 4.2 | 6.0 |
| total Ca | 1.00 ± 0.04 | 2.10 ± 0.04 | 3.30 ± 0.04 |
| ionized Ca | 0.75 ± 0.02 | 1.25 ± 0.02 | 1.75 ± 0.02 |
| Cl | 80 | 103 | 120 |
| protein | 70 g/l | 70 g/l | 70 g/l |
| Hepes (base form) | 30.6 | 41.0 | 50.0 |
| Hepes (acid form) | 25.3 | 24.5 | 15.0 |
| TMA | — | 7.3 | 12.0 |

All the concentrations are in millimol per liter, except protein (and pH, of course).

EXAMPLE III

The process of example I was repeated, except that after water KCl, $CaCl_2$ and NaCl had been added to 5 ml (for a final volume of 10 ml), 16.65 mg (for 19.8 mM/l of $NaHCO_3$ were weighed and added, and that said flushing with filtering and packing were done under a gas mixture of 95% of $N_2$ and 5% of $CO_2$. Its pH was 7.40 and it was calculated to contain 1.845 mmol/l of $CO_2$.

We claim:

1. A calibration liquid for use in calibrating apparatus used in analyzing blood components, said calibration liquid consisting essentially of an aqueous solution of sodium ion, potassium ion, calcium ion, chloride ion, albumin in a concentration of from 20 to 200 g/liter, and a partially neutralized nitrogen-containing organic sulfonic acid, said calibration liquid having a pH of 7.2 to 7.6.

2. Calibration liquid according to claim 1, wherein said nitrogen-containing organic sulfonic acid is 2-[4-(2-hydroxyethyl)piperazino]ethane sulfonic acid.

3. Calibration liquid according to claim 1, wherein said nitrogen-containing organic sulfonic acid is N-[tris(hydroxymethyl)methyl]-2-aminoethane sulfonic acid.

4. Calibration liquid according to claim 1, wherein said calibrating liquid comprises a series of three solutions, one of them containing the components at concentrations of about those in the blood from a normal, healthy individual, one of them containing the components at concentrations of about the lowest values that might be encountered and one of them containing the components at concentrations of about the highest values that might be encountered.

5. Calibration liquid according to claim 4, wherein said three solutions have the following compositions:

| Component | low level | normal | high level |
| --- | --- | --- | --- |
|  | concentrations in mmol/liter |  |  |
| $Na^+$ | 120 | 140 | 160 |
| $K^+$ | 3.0 | 4.2 | 6.0 |
| $Ca^{2+}$ total | 1.0 | 2.1 | 3.3 |
| free, ionized $Ca^{2+}$ | 0.75 | 1.25 | 1.75 |
| $Cl^-$ | 80 | 100 | 120 |
| pH | 7.2 | 7.4 | 7.6 |
| Total protein | 70 g/l | 70 g/l | 70 g/l |

6. Calibration liquid according to claim 1, wherein said calibration liquid contains between 120 and 160 mmol/liter of sodium, between 3.0 and 6.0 mmol/liter of potassium, between 1.0 and 3.3 mmol/liter of total calcium, and between 80 and 120 mmol/liter of chloride.

7. Process for preparing a calibration liquid comprising the steps of (1) preparing an aqueous solution consisting essentially of sodium ion, potassium ion, calcium ion, chloride ion, a partially neutralized nitrogen-containing organic sulfonic acid, and albumin in a concentration of 20 to 200 g/liter, and (2) adjusting the pH of said aqueous solution to between 7.2 and 7.6.

8. Process for preparing a solid material which can be used to prepare a calibration liquid for use in calibrating apparatus used in analyzing blood components, said process comprising the steps of (1) preparing an aqueous solution consisting essentially of sodium ion, potassium ion, calcium ion, chloride ion, a partially neutralized nitrogen-containing organic sulfonic acid, and albumin in a concentration of 20 to 200 g/liter, (2) adjusting the pH of said aqueous solution to between 7.2 and 7.6, and (3) removing the water from said aqueous solution.

9. A method of calibrating an ion-specific electrode used for analyzing blood components comprising the step of contacting said ion-specific electrode with an aqueous solution consisting essentially of sodium ion, potassium ion, calcium ion, chloride ion, a partially neutralized nitrogen-containing organic sulfonic acid, and albumin in a concentration of 20 to 200 g/liter, and said aqueous solution having a pH of 7.2 to 7.6.

10. A calibration liquid for use in calibrating apparatus used in analyzing blood components, said calibration liquid consisting essentially of an aqueous solution of sodium ion, potassium ion, calcium ion, chloride ion, albumin in a concentration of from 20 to 200 g/liter, globulins, and a partially neutralized nitrogen-containing organic sulfonic acid, said calibration liquid having a pH of 7.2 to 7.6.

11. Calibration liquid according to claim 10, wherein said nitrogen-containing organic sulfonic acid is 2-[4-(2-hydroxyethyl)piperazino]ethane sulfonic acid.

12. Calibration liquid according to claim 10, wherein said nitrogen-containing organic sulfonic acid is N-[tris(hydroxymethyl)methyl]-2-aminoethane sulfonic acid.

13. Process for preparing a calibration liquid comprising the steps of (1) preparing an aqueous solution consisting essentially of sodium ion, potassium ion, calcium ion, chloride ion, a partially neutralized nitrogen-containing organic sulfonic acid, albumin in a concentration of 20 to 200 g/liter, and globulins, and (2) adjusting the pH of said aqueous solution to between 7.2 and 7.6.

14. Process for preparing a solid material which can be used to prepare a calibration liquid for use in calibrating apparatus used in analyzing blood components, said process comprising the steps of (1) preparing an aqueous solution consisting essentially of sodium ion, potassium ion, calcium ion, chloride ion, a partially neutralized nitrogen-containing organic sulfonic acid, albumin in a concentration of 20 to 200 g/liter, and globulin, (2) adjusting the pH of said aqueous solution to between 7.2 and 7.6, and (3) removing the water from said aqueous solution.

15. A method of calibrating an ion-specific electrode used for analyzing blood components which includes the step of contacting said ion-specific electrode with an aqueous solution consisting essentially of sodium ion, potassium ion, calcium ion, chloride ion, a partially neutralized nitrogen-containing organic sulfonic acid, albumin in a concentration of 20 to 200 g/liter, and globulins, and said aqueous solution having a pH of 7.2 to 7.6.

16. A calibration liquid for use in calibrating apparatus used in analyzing blood components, said calibration liquid consisting essentially of an aqueous solution of sodium ion, potassium ion, calcium ion, chloride ion, bicarbonate ion, carbon dioxide, albumin in a concentration of 20 to 200 g/liter, and a partially neutralized nitrogen-containing organic sulfonic acid, said calibration liquid having a pH of 7.2 to 7.6.

17. A solid material suitable for preparing a calibration liquid for use in calibrating apparatus used in analyzing blood components, said solid material consisting essentially of sodium chloride, potassium chloride, calcium chloride, albumin and a partially neutralized nitrogen-containing organic sulfonic acid, wherein said solid material when reconstituted to an albumin concentration of from 20 to 200 g/liter has a pH of 7.2 to 7.6.

* * * * *